(12) United States Patent
Takenaga et al.

(10) Patent No.: US 7,968,600 B2
(45) Date of Patent: Jun. 28, 2011

(54) MEDICAMENT FOR PREVENTIVE AND THERAPEUTIC TREATMENT OF PHYSICAL DYSFUNCTION CAUSED BY NERVE DAMAGE

(75) Inventors: Mitsuko Takenaga, Kanagawa (JP); Koichi Shudo, Tokyo (JP); Tetsuro Matsuishi, Saitama (JP); Miwako Ishido, Tokyo (JP)

(73) Assignees: Nanoegg Research Laboratories, Inc., Kanagawa (JP); Kemphys Ltd., Tokyo (JP)

( * ) Notice: Subject to any disclaimer, the term of this patent is extended or adjusted under 35 U.S.C. 154(b) by 1154 days.

(21) Appl. No.: 11/670,126

(22) Filed: Feb. 1, 2007

(65) Prior Publication Data

US 2008/0182905 A1     Jul. 31, 2008

(30) Foreign Application Priority Data

Jan. 29, 2007   (JP) ................. 2007-017401

(51) Int. Cl.
| | |
|---|---|
| *A01N 37/10* | (2006.01) |
| *A01N 31/04* | (2006.01) |
| *A01N 37/18* | (2006.01) |
| *A01N 37/12* | (2006.01) |
| *A01N 37/44* | (2006.01) |
| *A61K 31/19* | (2006.01) |
| *A61K 31/07* | (2006.01) |
| *A61K 31/16* | (2006.01) |
| *A61K 31/195* | (2006.01) |

(52) U.S. Cl. ......... 514/568; 514/725; 514/613; 514/563
(58) Field of Classification Search .................. 514/568, 514/725, 613, 563
See application file for complete search history.

(56) References Cited

OTHER PUBLICATIONS (Takeshita, 1996, Ann Intern Med, 124, 893-896).*
R. Evans, "The Steroid and Thyroid Hormone Receptor Superfamily", Science, vol. 240, pp. 889-895 (1988).
M. Petkovich et al., "A Human Retinoic Acid Receptor Which Belongs to the Family of Nuclear Receptors", Nature, vol. 330, pp. 444-450 (1987).
Y. Hashimoto et al. "Retinobenzoic Acids and Nuclear Retinoic Acid Receptors", Cell Structure and Function, vol. 16, pp. 113-123 (1991).
Y. Hashimoto et al. "Expression of Retinoic Acid Receptor Genes and the Ligand-Binding Selectivity of Retinoic Acid Receptors (RAR'S)", Biochem. Biophys. Res. Commun., vol. 166, No. 3, pp. 1300-1307 (1990).
K. Hunter et al. "Retinoic Acid Stimulates Neurite Outgrowth in the Amphibian Spinal Cord", Proc. Natl. Acad. Sci., vol. 88, pp. 3666-3670 (1991).
L. Wuarin et al., "Retinoids Increase Perinatal Spinal Cord Neuronal Survival and Astroglial Differentiation", Int. J. Devl. Neuroscience, vol. 8, No. 3, pp. 317-326 (1990).
B. Haskell et al., "Effect of Retinoic Acid on Nerve Growth Factor Receptors", Cell Tissue Res., vol. 247, pp. 67-73 (1987).
S. D. P. Quinn et al., "Enhanced Neuronal Regeneration by Retinoic Acid of Murine Dorsal Root Ganglia and of Fetal Murine and Human Spinal Cord in Vitro", In Vitro Cell. Dev. Biol., vol. 27 A, pp. 55-62 (1991).
J. Mey, "New Therapeutic Target for CNS Injury? The Role of Retinoic Acid Signaling after Nerve Lesions", J. of Neurobiol., vol. 66, pp. 757-779 (2006).
M. O. Taha et al., "Effect of Retinoic Acid on Tibial Nerve Regeneration After Anastomosis in Rats: Histological and Functional Analyses", Transpl. Proc., vol. 36, pp. 404-408 (2004).

* cited by examiner

*Primary Examiner* — Sreeni Padmanabhan
*Assistant Examiner* — Umamaheswari Ramachandran
(74) *Attorney, Agent, or Firm* — Greenblum & Bernstein, P.L.C.

(57) ABSTRACT

A medicament for preventive and/or therapeutic treatment of a physical dysfunction such as motor dysfunction caused by nerve damage resulting from an accident, cerebral crisis and the like, which comprises as an active ingredient a compound or a salt thereof represented by the following general formula (I):

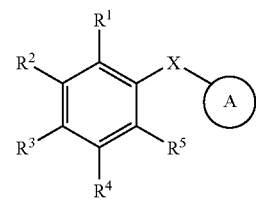

wherein $R^1$ to $R^5$ represents hydrogen atom, an alkyl group, or an alkyl-substituted silyl group, X represents —CONH— or —NHCO—, and A represents a carboxylic acid-substituted aromatic group which may be substituted or a tropolonyl group which may be substituted.

3 Claims, 1 Drawing Sheet

MEDICAMENT FOR PREVENTIVE AND THERAPEUTIC TREATMENT OF PHYSICAL DYSFUNCTION CAUSED BY NERVE DAMAGE

TECHNICAL FIELD

The present invention relates to a medicament for preventive and therapeutic treatment of physical dysfunction such as motor dysfunction caused by nerve damage resulting from an accident, cerebral crisis and the like.

BACKGROUND ART

Nerve damages by physicogenic causes such as accidents, or nerve damages caused by diseases such as acute ischemic cerebral diseases often causes physical dysfunctions such as motor dysfunctions including paralysis and lalopathy. For example, the number of patients of apoplectic stroke such as cerebral hemorrhage and cerebral infarction is about 1.4 million in Japan. Cerebral nerves are damaged by severe stroke due to the brain hemorrhage or cerebral infraction, which often results in physical dysfunctions such as paralysis and lalopathy as remaining after-troubles.

Moreover, more than one million people in Japan live with some sort of paralysis in their bodies after injury on spinal cord due to traffic accidents and the like, and it has been reported that more than five thousand people with injured spinal cord are annually increased. When rupture, blunt trauma, or compression of the spinal cord is caused by spinal fracture or bruise, spinal nerve is damaged, thereby physical dysfunctions of whole or part of the body occurs, for example, paralysis or motor dysfunction, or sensory dysfunction, autonomic disorder, or dysuria/dyschezia. Since main causes of the spinal cord injuries are traffic and sport accidents, a serious problem has arisen because many young people are bedridden or condemned to live with wheelchairs. For such physical dysfunctions caused by the nerve damage, early rehabilitation is performed as treatment to maintain remaining functions. However, no radical therapy for the physical dysfunctions caused by nerve damage has been developed, and therefore development of an effective therapeutic method has been highly desired.

It has been revealed that the retinoic acid receptor (RAR) present in cellular nucleus, which belongs to the intranuclear receptor super family (Evans, R. M., Science, 240, p. 889, 1988), regulates proliferation and differentiation of animal cells or cellular mortalities via binding with a ligand (Petkovich, M., et al., Nature, 330, pp. 444-450, 1987). A ligand for the RAR that naturally exist in a living body is all-trans retinoic acid (Vitamin A acid) which is an active metabolite of Vitamin A.

It has also been suggested that compounds having retinoic acid-like biological activities (e.g., 4-[(5,6,7,8-tetrahydro-5,5,8,8-tetramethyl-2-naphthalenyl)carbamoyl]-benzoic acid: Tamibarotene) also bind to RAR in similar manners to retinoic acid to exhibit their physiological actions (Hashimoto, Y., Cell Struct. Funct., 16, pp. 113-123, 1991; Hashimoto, Y., et al., Biochem. Biophys. Res. Commun., 166, pp. 1300-1307, 1990). Experimentally by using animals and clinically, these compounds have been found to be useful for therapeutic and preventive treatments of vitamin A deficiency disease, hyperkeratosis of epithelial tissue, rheumatism, delayed allergy, bone diseases, leukemia, and certain types of cancer.

Vitamin A and its derivatives are known to be involved in the differentiation of nerve cells during fetal and growth periods (Hunter, K. et al., Proc. Natl. Acad. Sci. USA, 88, p. 3666, 1991; Wuarin, L. et al., Int. J. Dev. Neurosci., 8, p. 317, 1990; Haskell, B. E. et al., Cell Tissue Res., 247, p. 67, 1987, Quinn, S. D. P. et al., In Vitro Cell Dev. Biol., 27A, p. 55, 1991) A review article on the effect of retinoic acid to nerves was written by Mey et al. (Mey, J., J Neurobiol., 66, p. 757, 2006).

Mey, however, explains in the above publication that no report was made that clearly demonstrates a therapeutic effect of Vitamin A acid in animals with damaged nerves. For example, in a tibial nerve transaction model, although Vitamin A acid at 50 µL (10 nM RA) induced 30% increase of regenerated nerves, no recovery in nerve and motor functions was reported to be achieved (Taha, M.O. et al., Trabspl. Proc., 36, p.404, 2004). As explained above, it is suggested that Vitamin A acid or RAR signal transmission system is in some way involved in the differentiation of nerve cells. However, it has not yet been clarified whether or not activation of such pathways successfully achieves recovery of motor dysfunction caused by nerve damage. In order to achieve recovery from higher neurological symptoms such as in motor and sensory functions, environmental arrangements around nerve cells including glial cells and neurotrophic factors, as well as the regeneration of neurons, are essential. From the aforementioned findings, it still remains unknown whether or not Vitamin A acid is capable of achieving nerve regeneration and improvement of motor function together with improvement of the aforementioned environments.

Non-patent document 1: Proc. Natl. Acad. Sci. USA, 88, p.3666, 1991

Non-patent document 2: Int. J. Dev. Neurosci., 8, p.317,1990

Non-patent document 3: Cell Tissue Res., 247, p.67, 1987

Non-patent document 4: In Vitro Cell Dev. Biol., 27A, p.55, 1991

Non-patent document 5: J. Neurobiol., 66, p.757, 2006

Non-patent document 6: Trabspl. Proc., 36, p.404, 2004

DISCLOSURE OF THE INVENTION

Object to be Achieved by the Invention

An object of the present invention is to provide a medicament for preventive and therapeutic treatment of physical dysfunction such as motor dysfunction caused by nerve damage resulting from an accident, cerebral crisis and the like.

Means to Achieve the Object

The inventors of the present invention conducted various researches to achieve the foregoing object. As a result, they found that compounds such as 4-[(5,6,7,8-tetrahydro-5,5,8,8-tetramethyl-2-naphthalenyl)carbamoyl]benzoic acid had an action of remarkably improving motor functions in model animal with spinal injury, and had excellent properties as an active ingredient of a medicament for preventive and/or therapeutic treatment of physical dysfunctions such as motor dysfunction caused by nerve damage resulting from an accident, cerebral crisis and the like. The present invention was achieved on the basis of the above findings.

The present invention thus provides a medicament for preventive and/or therapeutic treatment of a physical dysfunction caused by a nerve damage, which comprises as an active ingredient a compound or a salt thereof represented by the following general formula (I):

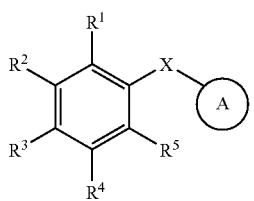

wherein $R^1$, $R^2$, $R^3$, $R^4$, and $R^5$ each independently represents hydrogen atom, a lower alkyl group, or a lower alkyl-substituted silyl group, and when any two adjacent groups of $R^1$, $R^2$, $R^3$, $R^4$, and $R^5$ are lower alkyl groups, the two groups may combine to form a 5- or 6-membered ring together with the carbon atoms on the benzene ring to which the groups bind (said ring may have one or more alkyl groups), X represents —CONH— or —NHCO—, and A represents a carboxylic acid-substituted aromatic group which may be substituted or a tropolonyl group which may be substituted.

According to preferred embodiments of the above invention, provided are the aforementioned medicament wherein the physical dysfunction is motor dysfunction, sensory dysfunction, or autonomic dysfunction; the aforementioned medicament wherein the nerve damage is caused by central nerve dysfunction; the aforementioned medicament wherein the central nerve dysfunction is spinal dysfunction or cerebral dysfunction; and the aforementioned medicament wherein the nerve damage is a structural nerve damage.

From another aspects, provided are use of the compound or a salt thereof represented by the above general formula (I) for manufacture of the aforementioned medicament; and a method for preventive and/or therapeutic treatment of a physical dysfunction caused by a nerve damage comprising the step of administering an effective amount of the compound represented by the above general formula or a salt thereof to a mammal including a human.

BEST MODE FOR CARRYING OUT THE INVENTION

Figure 1:
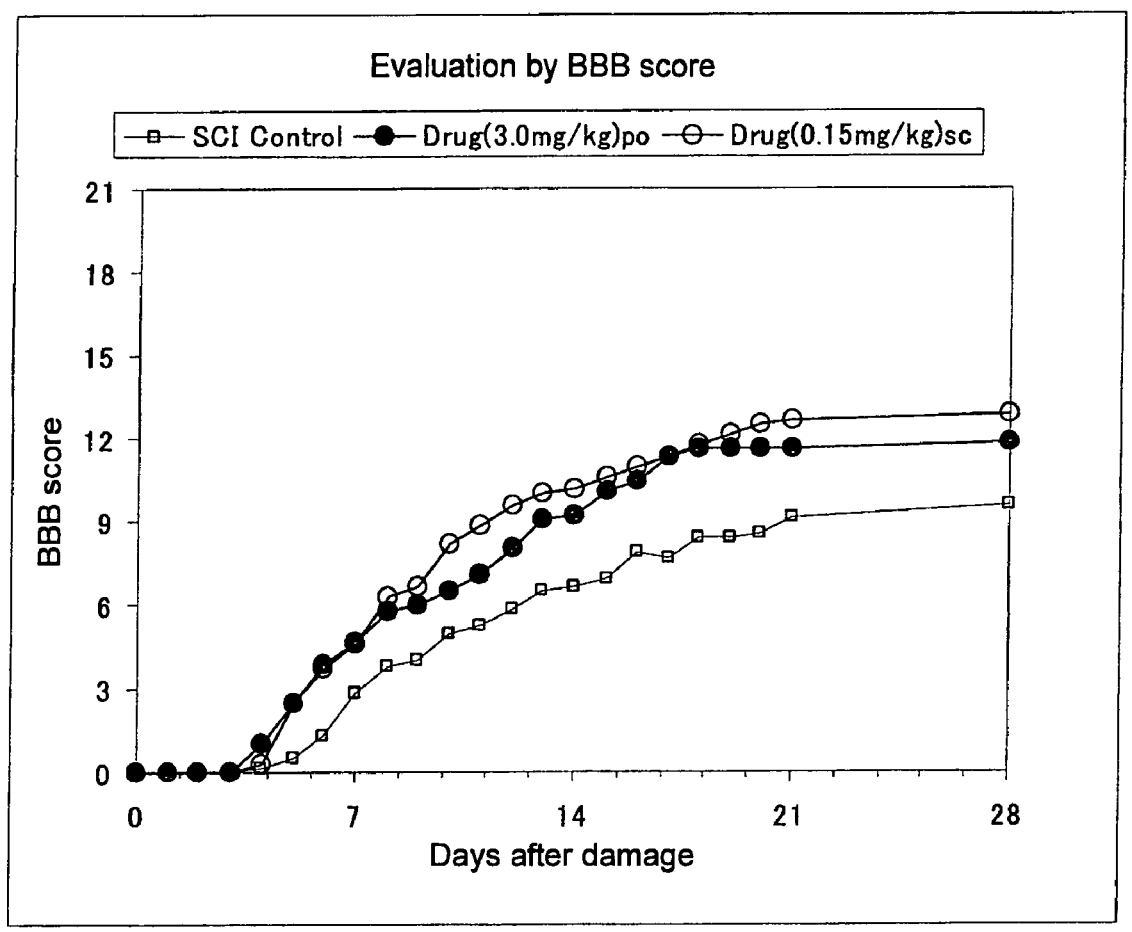
FIG. 1 depicts the effect of the medicament of the present invention, wherein ●: 1st group, orally administered with 3 mg/kg of 4-[(5,6,7,8-tetrahydro-5,5,8,8-tetramethyl-2-naphthalenyl)carbamoyl]benzoic acid; ○: 2nd group, subcutaneously administered with 0.15 mg/kg of 4-[(5,6,7,8-tetrahydro-5,5,8,8-tetramethyl-2-naphthalenyl)carbamoyl]benzoic acid; □: 3rd group, a control group orally administered with 0.5% CMC.

In the aforementioned general formula (I), as the lower alkyl group represented by $R^1$, $R^2$, $R^3$, $R^4$, and $R^5$, a linear or branched alkyl group having about 1 to 6, preferably 1 to 4, carbon atoms may be used. For example, methyl group, ethyl group, n-propyl group, isopropyl group, n-butyl group, sec-butyl group, or tert-butyl group may be used. On the aforementioned lower alkyl group, one or more of any kinds of substitutents may exist. As the substitutent, for example, hydroxy group, a lower alkoxy group, and a halogen atom can be exemplified. As the lower alkyl substituted-silyl group represented by $R^1$, $R^2$, $R^3$, $R^4$, and $R^5$, an example includes trimethylsilyl group.

Any two adjacent lower alkyl groups selected from the group consisting of $R^1$, $R^2$, $R^3$, $R^4$, and $R^5$ may combine to form one or two, preferably one, 5- or 6-membered ring together with the carbon atoms on the benzene ring to which the groups bind. The ring thus formed may be saturated, partially saturated, or aromatic, and the ring may have one or more alkyl groups. As the alkyl group which may substitute on the ring, a linear or branched alkyl group having about 1 to 6, preferably 1 to 4, carbon atoms may be used. For example, methyl group, ethyl group or the like may be used, and the ring may be substituted with preferably 2 to 4, more preferably 4, methyl groups. For example, the benzene ring on which $R^2$ and $R^3$ substitute together with $R^2$ and $R^3$ may preferably form 5,6,7,8-tetrahydronaphthalene ring, 5,5,8,8-tetramethyl-5,6,7,8-tetrahydronaphthalene ring or the like.

As the carboxylic acid-substituted aromatic group represented by A, a phenyl group substituted with carboxylic acid or a heteroring group substituted with carboxylic acid. A phenyl group substituted with carboxylic acid is preferred, and 4-carboxyphenyl group is more preferred. Examples of a heterocyclic carboxylic acid for constituting the heteroring group substituted with carboxylic acid represented by A include, for example, pyrimidine-5-carboxylic acid and the like. As the tropolonyl group represented by A, tropolon-5-yl group is preferred. On the ring of the carboxylic acid-substituted aromatic group or tropolonyl group, one or more substitutents may exist. A type of the substitutent is not particularly limited. Examples include, for example, hydroxyl group, a halogen atom, amino group or the like.

As preferred compounds, for example, compounds comprising a phenyl-substituted carbamoylbenzoic acid or a phenyl-substituted carboxamidobenzoic acid as a basic skeleton can be used. A typical example of the compounds having a phenyl-substituted carbamoylbenzoic acid as a basic skeleton includes 4-[(5,6,7,8-tetrahydro-5,5,8,8-tetramethyl-2-naphthalenyl)carbamoyl]benzoic acid (see, Hashimoto, Y., Cell Struct. Funct., 16, pp. 113-123, 1991; Hashimoto, Y., et al., Biochem. Biophys. Res. Commun., 166, pp. 1300-1307, 1990), and a typical example of the compounds having a phenyl-substituted carboxamidobenzoic acid includes 4-[(3, 5-bis-trimethylsilylphenyl)carboxamido]benzoic acid (J. Med. Chem., 33, pp. 1430-1437, 1990). In the specification, the term "basic skeleton" means a main chemical structure for one or more arbitrary substitutents to bind thereto. A particularly preferred compound includes 4-[(5,6,7,8-tetrahydro-5, 5,8,8-tetramethyl-2-naphthalenyl)carbamoyl]benzoic acid.

As the active ingredient of the medicament of the present invention, salts of the aforementioned compounds may be used. For example, physiologically acceptable salts including metal salts such as sodium salts, potassium salts, magnesium salts, and calcium salts, ammonium salts, organic amine salts such as triethylamine salts, and ethanolamine salts, and the like can be used as the active ingredient of the medicament of the present invention. As the active ingredient of the medicament of the present invention, a prodrug of the aforementioned compound may be used. The term "prodrug" means a compound or a salt thereof which is, after oral or parenteral administration to an mammal, subjected to a structural change such as hydrolysis in vivo, preferably in blood, to produce the above compound or a salt thereof. For example, various means for producing prodrugs from pharmaceutical compounds having carboxylic acid, amino group, hydroxyl group or the like are known, and one of ordinary skill in the art can choose appropriate means. Types of the prodrug of compound or a salt thereof are not particularly limited. For example, where a compound has carboxylic acid, an example includes a prodrug wherein the carboxylic acid is converted into an alkoxycarbonyl group. Preferred examples include ester compounds such as methoxycarbonyl group or ethoxycarbonyl group.

The aforementioned compounds may have one or more asymmetric carbons depending on the types of substituents, and any optical isomers based on these asymmetric carbons, any mixtures of optical isomers, racemates, diastereoisomers based on two or more asymmetric carbons, any mixtures of diastereoisomers, and the like can be used as the active ingredient of the medicament of the present invention. Furthermore, geometrical isomers based on cis- or trans-configuration of double bond, any mixtures of geometrical isomers, and any hydrates or solvates of the compounds in free forms or in the form of a salt can also be used as the active ingredient of the medicament of the present invention.

The medicament of the present invention can be used for preventive and/or therapeutic treatment of a physical dysfunction such as motor dysfunction caused by a nerve damage. In the specification, the term "preventive and/or therapeutic treatment of a physical dysfunction" includes preventive treatments such as complete prevention of occurrence of physical dysfunction or prevention of occurrence of severe physical dysfunction to preserve as mild dysfunction, or therapeutic treatment for improvement or healing of already occurred physical dysfunction. As for effectiveness of the preventive and/or therapeutic treatment, the term should be construed in its broadest sense including improvement of findings diagnosed by a doctor and improvement of rational symptoms.

Examples of the physical dysfunction caused by nerve damage as used herein includes, for example, motor dysfunction, sensory dysfunction, or autonomic dysfunction caused by nerve damage. Examples of the nerve damage includes, for example, nerve damage in central nerve system including spinal cord and brain, or nerve damage in peripheral nerve system.

Examples of the neuronal damages in spinal cord include, for example, those caused by mechanical trauma (such as spinal cord injury due to dislocation and subluxation of vertebral body joint, fracture of the spine, spinal cord compression, disc hernia), by ischemia or ischemic-reperfusion (such as spinal cord ischemia and spinal paralysis due to extramedullary vascular dysfunction) or by neoplasm (such as spinal cord neoplasm, bone tumors of the spine).

Examples of the neuronal damage in brain include, for example, those caused by mechanical trauma (such as neuronal damage due to brain contusion or head injury), by ischemia or ischemic-reperfusion (such as stroke, cerebral infarction, brain hemorrhage, brain ischemia, subarachnoid hemorrhage, aneurysmal hemorrhage, myocardial infarction, hypoxia, or major epilepsy/cerebral ischemia caused by anoxia), or by neoplasm (such as brain tumor).

Examples of the neuronal damage in peripheral nerve system include, for example, those caused by neurotmesis due to trauma (such as blow or contusion), or nerve structural injury such as compression or crush.

Examples of the subjective or objective symptom of the motor dysfunction include, for example, partial or total paralysis, motor paralysis, numbness, pain, spasm, abnormal gait or movement (such as ataxic gait, paralytic gait, or gait disturbance), motor ataxia, abnormal involuntary movements, loss of the reflex, abnormal reflex, abnormal extensor reflex, abnormal posture, muscular hypertonia, myotonia, exaggerated deep tendon reflex, muscular hypotonia, myalgia, dysphagia or disorder of conversation (such as dysphasia, aphasia, dysarthria or alalia).

Examples of the subjective or objective symptom of the sensory dysfunction include, for example, numbness, coldness, pain, hyperesthesia (such as hypersensibility, tactile hyperesthesia or hyperaphia), loss of aesthesia, anesthesia, cutaneous sensory impairment, cognitive impairment, vertigo, disorder of the sense of smell, auditory hallucination, visual hallucination, emotional disorder, disorder of the voice (such as dysphonia or aphonia), disorder of speech or conversation (such as lalopathy or dysarthria in specific conversation, expressive lalopathy or recipient lalopathy), higher cerebral dysfunction (such as aphasia, unilateral spatial agnosia or frontal lobe syndrome).

Examples of the subjective or objective symptom of the autonomic disorder include, for example, decrease in cardiac function, vascular function, urination, reproductive function or gut function, and more specifically dyshidrosis, lightheadedness, constipation, diarrhea, decrease in gallbladder contractile function, sexual dysfunction, ED (erectile dysfunction), or respiratory paralysis.

The medicament of the present invention comprises, as an active ingredient, one or two or more substances selected from the group consisting of the aforementioned compound and a salt thereof, and a hydrate thereof and a solvate thereof. A preferred effectiveness may sometimes be obtained by administration of two or more different ingredients in combination. As the medicament of the present invention, the aforementioned substance, per se, may be administered. Preferably, the medicament can be administered as a pharmaceutical composition for oral or parenteral administration which can be prepared by a method well known to one of ordinary skill in the art.

As pharmaceutical compositions suitable for oral administration, examples include tablets, capsules, subtilized granules, granules, liquids, and syrups. As pharmaceutical compositions suitable for parenteral administration, examples include injections, suppositories, inhalant, eye drops, nasal drops, ointments, creams, and plasters. Examples of the parenteral administration also include, for example, local injection to a dysfunctional lesion, or under invasive or non-invasive operation, a method of spraying, applying, or attaching a solution to a dysfunctional lesion or damaged nerve, or circumstantial tissue. Administration may be performed via two or more different administration routes. Preferred forms of the medicament of the present invention include pharmaceutical compositions for oral administration, as well as pharmaceutical compositions in a form of injection suitable for local administration to a dysfunctional lesion or pharmaceutical compositions in a form of a solution suitable for topical application.

The aforementioned pharmaceutical composition can be prepared by addition of one or more physiologically and pharmacologically acceptable additives for formulation. Examples of the additives for formulation include, but not limited to, excipients, disintegrants or disintegration aids, binders, lubricants, coating agents, coloring agents, diluting agents, base materials, dissolving agents or dissolving aids, isotonizing agents, pH modifiers, stabilizers, propellants, and adhesives.

For example, for preparation of pharmaceutical compositions for oral administration such as tablets, capsules, granules, and powders, excipients such as lactose, crystalline cellulose, and starch, lubricants such as magnesium stearate and talc, binders such as hydroxypropylcellulose and polyvinylpyrrolidone, disintegrators such as carboxymethylcellulose calcium and low substituted hydroxypropyl methylcellulose, coating agents such as hydroxypropylmethylcellulose, macrogol, and silicone resin, and the like may be used as required.

A dose of the medicament of the present invention is not particularly limited. The dose may be suitably chosen depending on symptoms, age, body weight and the like of a patient, a method for administration, a type of active ingredient and the like. For example, for oral administrations, a dose of 0.01 to 1,000 mg, preferably 0.05 to 50 mg, more preferably 0.1 to 10 mg per day may be administered once or several times as divided portions. However, the aforementioned doses are only for examples, and the dose may be appropriately increased or decreased.

A period for administration is not particularly limited. The medicament may be administered in any period such as, for example, a method of preventive administration after injury but prior to occurrence of dysfunction, a method of administration immediately after subjective or objective observation of occurrence of dysfunction, or a method of therapeutic administration in a chronic state after occurrence of dysfunction. For example, administration may be performed in two or more of the aforementioned periods. A preferred example includes a method of continuous administration immediately after occurrence of dysfunction to a chronic state. The medicament of the present invention can be used in combination with other therapy for treatment of spinal injury such as cell therapy.

EXAMPLE

The present invention will be explained more specifically with reference to the example. However, the scope of the present invention is not limited to the following example.

Example 1

23 of 9 weeks old female Wistar rats had on their spinal cords of the thoracic vertebrae injured under anesthesia by loading a weight of 10 g dropped from a height of 2.5 cm to prepare traumatic spinal cord injury model rats with impaired motor function of the hind limb. The 23 rats were divided into the following 3 groups:
1st Group: 8 rats were administered orally with 3 mg/kg of 4-[(5,6,7,8-tetrahydro-5,5,8,8-tetramethyl-2-naphthalenyl)carbamoyl]benzoic acid once before the injury and then once a day.
2nd Group: 8 rats were administered with 0.15 mg/kg of 4-[(5,6,7,8-tetrahydro-5,5,8,8-tetramethyl-2-naphthalenyl)carbamoyl]benzoic acid directly to the injured site immediately after the injury, and then administered subcutaneously once a day near the injured area.
3rd Group: 7 rats were administered orally with 1 ml/kg of 0.5% carboxymethyl cellulose (CMC) solution as a control group.

Administration was performed every day for 21 days after the injury for each group. The motor function of the hind limb was evaluated according to the Basso-Beattie-Bresnahan (BBB) score every day up to 21st day, and 28th day after the injury. For animals with BBB scores being 10 or more, evaluation of the motor function was performed by using a treadmill (manufactured by Muromachi Kikai Co., Ltd) on the 21st and the 28th day. The treadmill tests were performed for 5 minutes with velocity of the treadmill walking surface being kept at 8 m/min. In the test, a period of time during which the animal walked with four legs was measured, and in addition, total number of the contact of the animal with the end wall of the walking surface due to the stop walking of the animal was measured, thereby motor function was evaluated.

As shown in FIG. 1, the group orally administered with 4-[(5,6,7,8-tetrahydro-5,5,8,8-tetramethyl-2-naphthalenyl)carbamoyl]benzoic acid and the group subcutaneously administered with 4-[(5,6,7,8-tetrahydro-5,5,8,8-tetramethyl-2-naphthalenyl)carbamoyl]benzoic acid gave significantly improved BBB scores compared to the control group, revealing an excellent improvement of the motor function of the hind limbs. In Table 1, results of the motor function on the 21st days from the injury evaluated by the compulsory walking using the treadmill and BBB scores are shown. In the treadmill test, prolongation of the walking period and remarkable decrease in the number of the contact with the back end wall, as compared to the control group, were observed in the group orally administered with 4-[(5,6,7,8-tetrahydro-5,5,8,8-tetramethyl-2-naphthalenyl)carbamoyl]benzoic acid and the group subcutaneously administered with 4-[(5,6,7,8-tetrahydro-5,5,8,8-tetramethyl-2-naphthalenyl)carbamoyl]benzoic acid, suggesting excellent improvements of motor function.

TABLE 1

| Groups | Speed: 8 (8 m/min) for 5 min | | |
|---|---|---|---|
| | walking time (min:sec) | Number of contact to back end wall | BBB score |
| Control group (administered with CMC) | 2:39 ± 0:37 | 48.3 ± 6.7 | 9.14 ± 1.83 |
| Group of oral administration at 3.0 mg/kg drug | 2:57 ± 1:17 | 16.0 ± 8.3(**) | 11.43 ± 3.80 |
| Group of subcutaneous administration at 0.15 mg/kg drug | 3:52 ± 0:39 | 13.4 ± 6.7(**) | 12.71 ± 2.28(*) |

(*p < 0.05, **p < 0.01)

INDUSTRIAL APPLICABILITY

The medicament of the present invention is useful for preventive and/or therapeutic treatment of physical dysfunction such as motor dysfunction caused by nerve damage resulting from an accident, cerebral crisis and the like.

What is claimed is:

1. A method for therapeutic treatment of spinal cord injury caused by nerve damage, which comprises administering to a mammal in need thereof a therapeutically effective amount of 4-[(5,6,7,8-tetrahydro-5,5,8,8-tetramethyl-2-naphthalenyl)carbamoyl]benzoic acid or a salt thereof.

2. The method according to claim 1, wherein the spinal cord injury is neuronal damage in the spinal cord.

3. The method according to claim 1, wherein the mammal is a human.

* * * * *